US007777187B2

(12) United States Patent
Cluff

(10) Patent No.: US 7,777,187 B2

(45) Date of Patent: Aug. 17, 2010

(54) APPARATUS AND METHOD FOR INVESTIGATING A SAMPLE

(75) Inventor: Julian A. Cluff, Cambridge (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 11/597,089

(22) PCT Filed: May 11, 2005

(86) PCT No.: PCT/GB2005/001801

§ 371 (c)(1), (2), (4) Date: Mar. 1, 2007

(87) PCT Pub. No.: WO2005/114295

PCT Pub. Date: Dec. 1, 2005

(65) Prior Publication Data

US 2007/0242274 A1 Oct. 18, 2007

(30) Foreign Application Priority Data

May 20, 2004 (GB) ................................ 0411271.0

(51) Int. Cl.
*G01N 21/35* (2006.01)

(52) U.S. Cl. .................................................. 250/341.1

(58) Field of Classification Search ............... 250/341.1
See application file for complete search history.

(56) References Cited

U.S. PATENT DOCUMENTS 4,502,751 A 3/1985 Fjeldsted et al.
4,778,984 A 10/1988 Nakamura
5,220,450 A 6/1993 Iizuka et al.
2002/0097386 A1 7/2002 Mishima
2003/0017858 A1 1/2003 Kraft et al.
2003/0149346 A1 8/2003 Arnone et al.
2003/0165003 A1* 9/2003 Ciesla et al. ................ 359/326
2004/0065832 A1 4/2004 Cluff et al.

FOREIGN PATENT DOCUMENTS

EP 0 553 781 8/1993
GB 1 501 908 2/1978
GB 2 174 196 10/1986

(Continued)

OTHER PUBLICATIONS

Tribe et al., "Hidden Object Detection: Security Applications of Terahertz Technology." Proc. SPIE, vol. 5354, Apr. 2004 pp. 168-176.

(Continued)

*Primary Examiner*—David P Porta
*Assistant Examiner*—Marcus H Taningco
(74) *Attorney, Agent, or Firm*—Dickstein Shapiro LLP

(57) ABSTRACT

An apparatus for investigating a sample comprising: a source of beam radiation; a detector for detecting a beam of radiation reflected by the sample and an optical subsystem for manipulating the beam between source and detector wherein the optical subsystem comprises a first optical element arranged in use to angularly deflect the source beam within a given solid angle and a second optical element arranged to focus the beam from the first optical element onto a substantially flat image plane and wherein radiation reflected by the sample passes back through the first and second optical elements to the detector.

13 Claims, 14 Drawing Sheets

31
29
23
35
27
37
29a
29b
39
25

FOREIGN PATENT DOCUMENTS

| | | |
|---|---|---|
| GB | 2 359 716 | 8/2001 |
| GB | 2 371 111 | 7/2002 |
| WO | WO 92/03187 | 3/1992 |

OTHER PUBLICATIONS

Kemp et al., “Security Applications of Terahertz Technology.” Proc. SPIE, vol. 5070, Aug. 2003, pp. 44-52.

Francis A. Jenkins, “Fundametals of Optics”, McGraw-Hill Education—Europe—Paperback—Sep. 1976, pp. 32-33.

Martin van Exter and Daniel R. Grischkowsky, IEEE Trans. Microwave Theory, vol. 38, No. 11, Nov. 1990.

Optical Scanning: Design and Applications, Proceedings of the Society of Photo-optical Instrumentation Engineers (SPIE) 3787, pp. 74-86, 1999.

* cited by examiner

53

Temporal 55
57
59

Temporal

APPARATUS AND METHOD FOR INVESTIGATING A SAMPLE

This invention relates to the field of investigating and imaging samples and also imaging methods. More specifically, the invention is concerned with such apparatus which use frequencies in the range overlapping the infrared and microwave parts of the spectrum. This frequency range encompasses the so-called Terahertz (THz) frequency range and is often referred to as Terahertz radiation.

Terahertz radiation roughly equates to frequencies in the range 25 GHz to 100 THz, particularly those frequencies in the range of 50 GHz to 84 THz, more particularly those in the range from 90 GHz to 50 THz and especially those in the range from 100 GHz to 20 THz.

Recently, there has been considerable interest in THz pulse imaging (TPI) which is showing promising results for both medical and non-medical use. THz radiation is non ionising radiation. Therefore, it is believed to be medically safer than well established x-ray techniques. The lower power levels used (nW to μW) also suggest that heating effects are not problematic, as may be the case with microwaves for example. THz pulse imaging uses a plurality of frequencies within a single pulse in order to probe the frequency dependent absorption characteristics of the sample under test.

THz continuous wave imaging systems are also known, see for example GB2359716.

Figure 3:
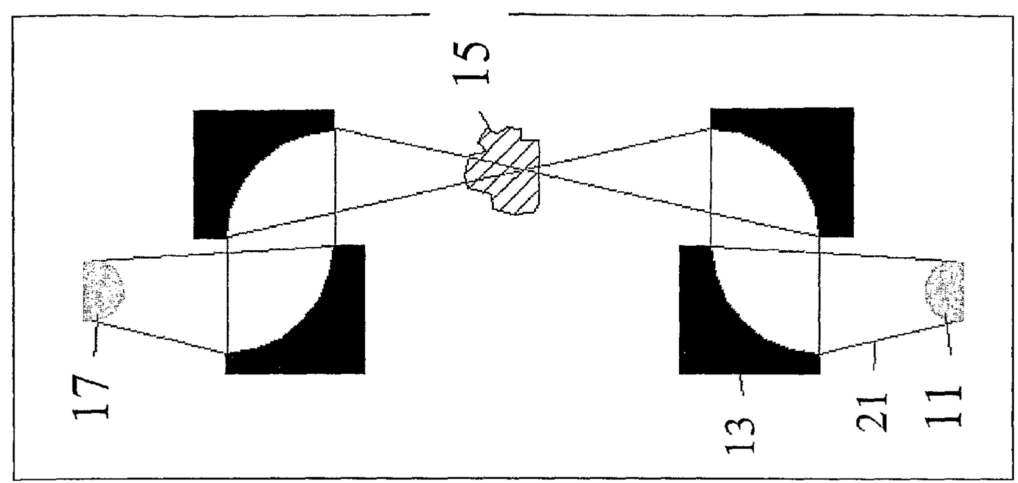

Generally, in order to maintain an acceptable signal to noise ratio, the imager system geometries are such that, for transmission based systems, there is a direct optical path from the radiation emitter to the detector when the sample is not present (see, for example, FIG. 2) and, for reflection systems, the radiation detectors are designed to directly intercept specularly reflected radiation (see FIG. 3).

The above design constraints mean that the emitted radiation beam cannot simply be steered by a fast moving mirror as neither directly transmitted or specularly reflected radiation would be detected at the detector. Additionally such an approach would result in curvature of the image plane which would correspondingly complicate imaging.

Existing scanning imaging systems either move the sample through the imaging beam or laterally move the focussing optics. The latter approach is described in GB 2371111. Both of these methods however require the reciprocating movement of relatively large and massive objects which thereby places restrictions on the rate at which an image can be acquired.

Rotation of the focussing optics would also require rapid movement of relatively massive objects followed by lateral translation of the optics and/or the sample in order to image the entire object. Additionally such approaches tend to rescan areas during a scan thereby reducing the efficiency of the system to as low as 50%.

Electromagnetic radiation is a wave phenomena and hence it is characterised by both phase and amplitude. Thus information regarding the sample can be measured by measuring changes in the amplitude and phase of the imaging radiation that is used. The phase is related to the propagation path length or propagation time of the radiation.

Since imaging is made by such an inherently phase sensitive technique, prior art imaging systems have also focussed on increasing the rate at which the phase may be scanned as an alternative way in which imaging acquisition times can be improved.

Many THz imaging systems rely on optical delay lines (in the visible region of the e/m spectrum) to acquire phase information. Since visible optics are smaller and lighter than THz optics scanning of the phase is usually easier and faster than scanning of the sample or of the beam. Consequently, such systems tend to acquire a phase data set at a fixed location before proceeding to a second location to acquire a second data set. This equates to scanning through the depth of the sample at a particular location (i.e. a section of the sample along the axis of the imaging beam is scanned). The ability therefore to scan perpendicular to the beam at a fixed depth would be beneficial.

It is therefore an object of the present invention to alleviate, or partially mitigate some of the problems associated with the prior art. In particular, it is an aim of the present invention to provide an apparatus which allows rapid scanning of a sample.

According to a first aspect of the present invention there is provided an apparatus for investigating a sample comprising: a source of beam radiation; a detector for detecting a beam of radiation reflected by the sample; and an optical subsystem for manipulating the beam between source and detector wherein the optical subsystem comprises a first optical element arranged in use to angularly deflect the source beam within a given solid angle and a second optical element arranged to focus the beam from the first optical element onto a substantially flat image plane and wherein radiation reflected by the sample passes back through the first and second optical elements to the detector.

The invention according to the first aspect of the present invention provides for an apparatus which comprises an optical sub-system capable of scanning the irradiating source beam without the requirement for the translation or rotation of large and massive objects. The position of the source beam when it scans the sample is effectively determined by the first optical element within the optical subsystem which is capable of angularly deflecting the source beam so that it is not necessary to move either the sample or the focussing optics in their entirety in order to scan the sample. As a consequence only one optical element is involved in beam steering and therefore the beam can be scanned more efficiently and more quickly than in prior art systems.

The second optical element in the sub-system serves to focus the angularly deflected source beam onto a substantially flat image plane. As a result it is possible to perform imaging of a sample at fixed depths within the sample.

The radiation reflected by the sample passes back through the optical subsystem to the detector thereby conforming to the imager system geometries mentioned above.

The invention according to the first aspect of the present invention images the sample under investigation by detecting reflected radiation from the sample. However, radiation may also be transmitted through the sample and therefore in a second aspect of the present invention there is provided an apparatus for investigating a sample comprising: a source of beam radiation; a detector for detecting a beam of radiation transmitted through the sample; and an optical subsystem for manipulating the beam between source and detector wherein the optical subsystem comprises a first optical element arranged in use to angularly deflect the source beam within a given solid angle; a second optical element arranged to focus the beam from the first optical element onto a substantially flat image plane; and a further optical element arranged to direct transmitted radiation onto the detector.

The invention according to the second aspect of the present invention is configured for transmitted radiation. Conveniently, the further optical element comprises third and fourth optical elements which are duplicates of the first and second optical elements, i.e. about the image plane the third optical element is a mirror image of the second optical element and the fourth optical element is a mirror image of the first optical element, the second and third optical elements being equivalent and the first and fourth optical elements being equivalent.

[Note: for the avoidance of doubt further features of both the first and second aspects of the present invention are discussed below]

THz imaging is inherently phase sensitive and so preferably, the detector measures a change in a phase dependent quantity of the radiation This might be a direct measurement of the phase itself, or a measurement of the electric field which is transmitted through or reflected from the sample, the amplitude of which will be phase dependent etc.

In order for the detector to be able to detect the phase dependent quantity with respect to the radiation which irradiates the sample, the detector needs to have some way of knowing information about the phase of the radiation which irradiates the sample. A convenient way to achieve this is for the detector to receive a probe beam which has a phase related to that of the radiation which is used to irradiate the sample.

The probe beam could be obtained by splitting the one or more of the input beams or it could be provided by splitting the Terahertz beam used to irradiate the sample. The detector could directly detect the probe beam or the probe beam could be combined with the radiation which has been transmitted through or reflected from the sample before detection. This combining of the two beams could be achieved by using a mixing component.

In order to detect the phase dependent quantity, the apparatus further preferably comprises a phase control means, which can be used to control the phase of the probe beam or the beam of radiation which irradiates the sample. The phase control means may be provided by an optical delay line which varies the length of the path of the probe beam with respect to the length of the path of the irradiating radiation. Of course, the length of the path of the irradiating radiation could be varied with respect to the length of the path of the probe beam to achieve the same result.

The length of the path of the probe beam can be varied during the imaging process to obtain information relating to the phase of the detected radiation.

Conveniently, the first optical element is a Risley (or Herschel) prism. Such devices are well known to ophthalmologists and comprise two thin prisms of equal power which are placed serially in the path of a light beam. The operation of such devices is discussed in Fundamentals of Optics (Fundamentals of Optics, Francis A. Jenkins; McGraw-Hill Education—Europe—Paperback—September 1976; Pages 32-33) and also in WO9203187. The Risley prism basically equates to a single prism of variable power and depending on the exact orientation of its two constituent prisms the light beam can be deflected within a certain solid angle.

The two prisms are arranged such that the planes bisecting the apex angle of each prism are essentially parallel. Incident light impinges onto the prism arrangement such that it is substantially normal to these planes. When the two prisms are arranged such that their thin ends are together then maximum deflection will occur (roughly twice the deflection of each individual prism). When the prisms are arranged such that the thin ends oppose one another then the light will not be substantially deviated. By varying the exact orientation of the two prisms relative to one another the incident light beam may be deflected in any direction within the solid angle defined by the maximum deflection. Usually there will be a small air gap between the two prisms to avoid friction effects and to prevent scratching.

One or both of the individual prisms of the Risley prism element may be rotatable. Preferably, in the event that both prisms rotate they can conveniently rotate independently of one another. However, the individual prisms of the Risley prism device can also be mechanically locked together to perform a specifically oriented scan.

Conveniently, the prisms can be rotated to provide a wide variety of scan modes from lateral movement of the scanning beam across the sample to spiral scanning.

The prisms can be rotated by any convenient means including cog, belt or tooth belt drives. The drive mechanism may conveniently be a DC motor. Preferably the drive mechanism is for the prism holder to form the drive motor itself and to be under computer control. Such an arrangement is compact, efficient and versatile.

The second optical element is conveniently a telecentric lens. Such a lens can be made from any suitable combination of optical elements or lenses such as aspheric, GRIN or Fresnel. For THz imaging suitable optical materials include HDPE, TPX, z-cut quartz or silicon.

Alternatively, a flat field lens may be used as the second optical element.

Other devices could be used to angularly scan the beam including galvanometers, spinning mirrors, spinning polygons, or solid state devices such as acousto- or electro-optic modulators.

Alternatively the Risley prism could be replaced by a dispersive prism or grating. In such a case the angular distribution of the radiation would be a function of frequency and the spatial distribution could be analysed by Fourier transform of the temporal trace. Although the data analysis in this configuration would be more intensive than using any of the other elements above it would have the benefit of no moving parts.

In a third aspect of the present invention there is provided a method for investigating a sample comprising the steps of irradiating the sample with a source of radiation with a frequency in the range 25 GHz to 100 THz, the radiation capable of being focussed at any given point within a plane through the sample, said plane being substantially normal to the direction of the irradiating radiation, and detecting said radiation reflected from or transmitted by the sample According to the above method the sample to be investigated can be imaged at a fixed depth. Preferably, an optical subsystem as described above is used to steer the irradiating radiation. Conveniently, such a subsystem also allows rapid scanning of the irradiating beam over the sample.

Figure 1:
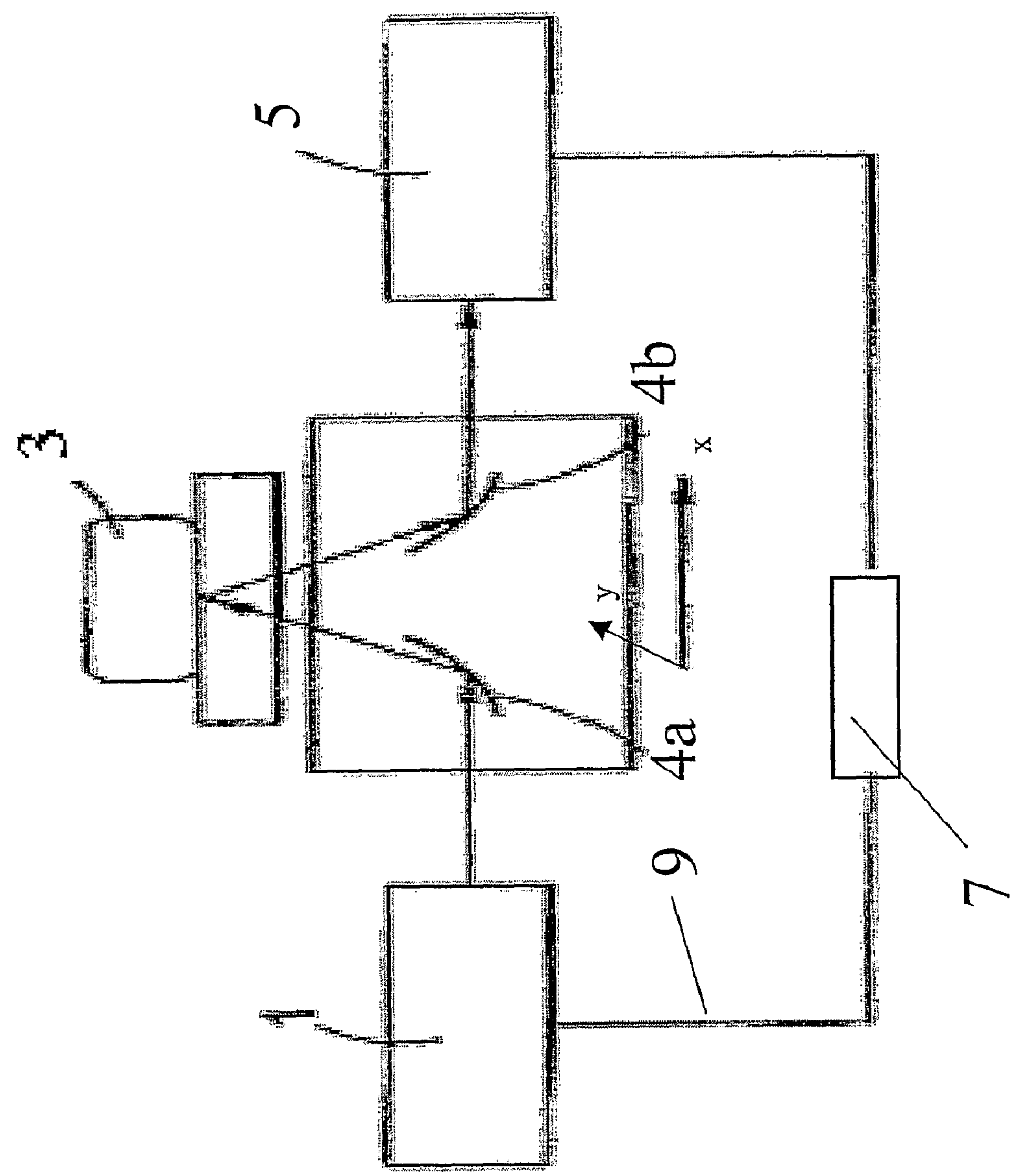

The present invention will now be described with reference to the following non-limiting preferred embodiments in which:

FIG. 1 shows a schematic of a typical THz imaging system

Figure 2:
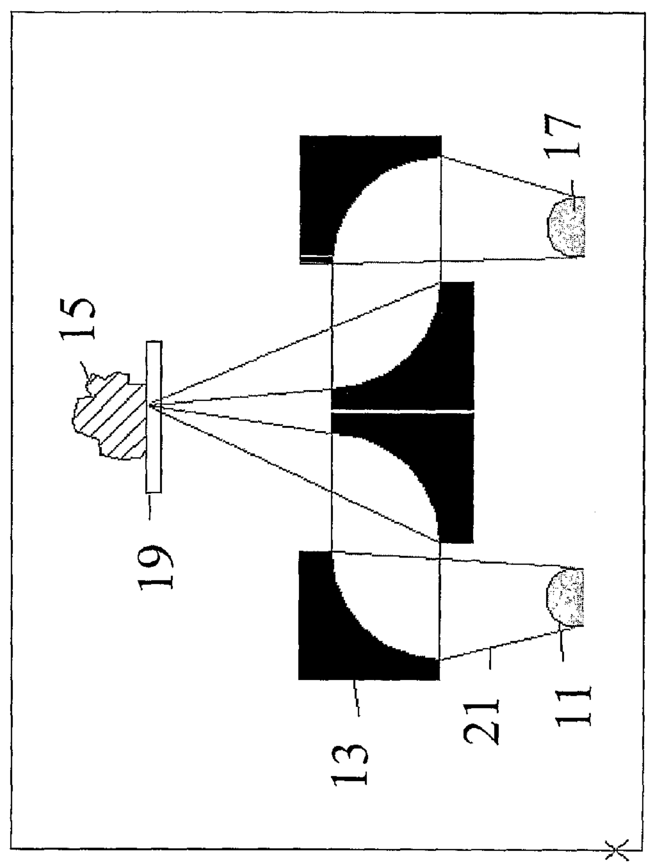
Figure 4A:
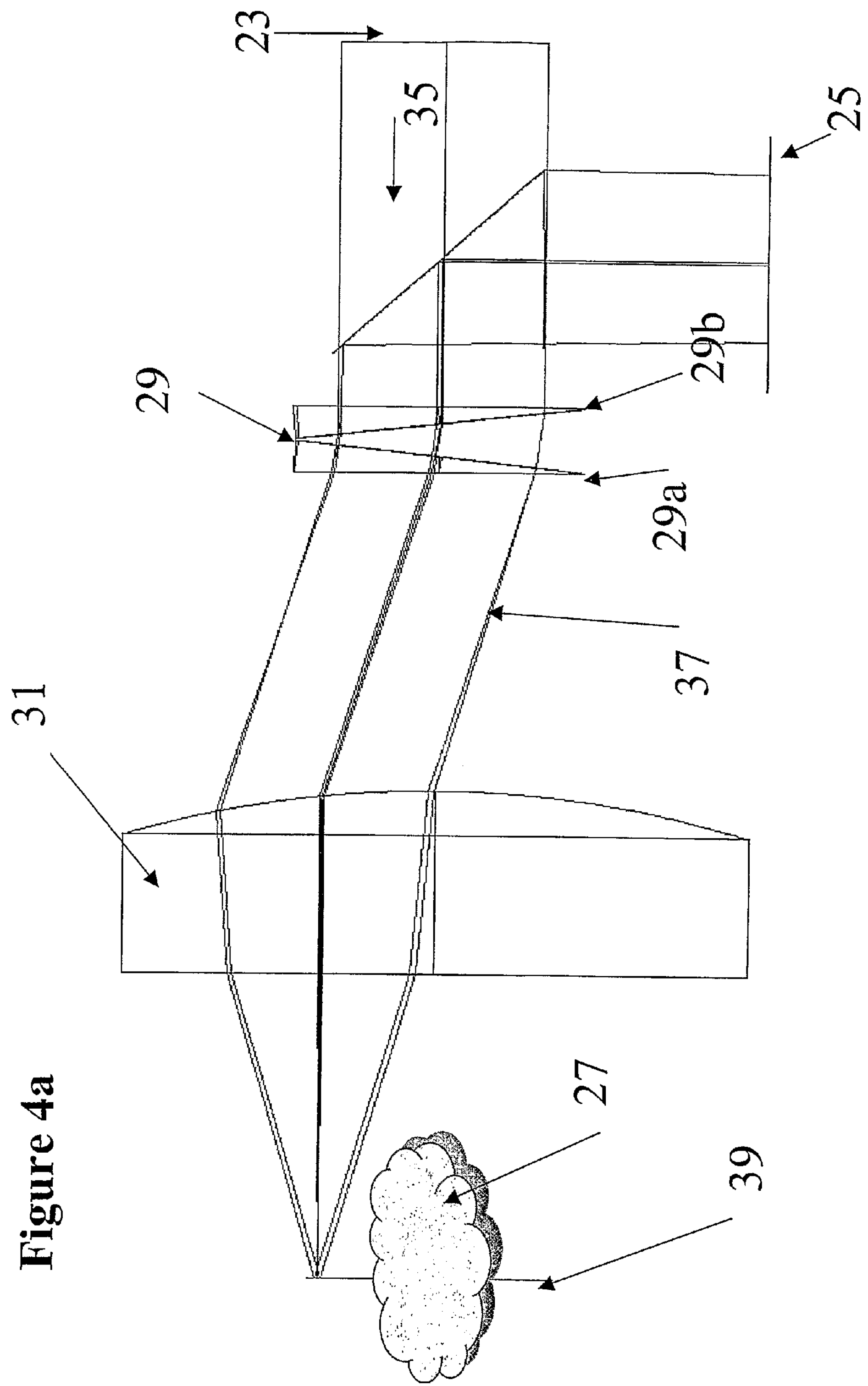
Figure 4B:
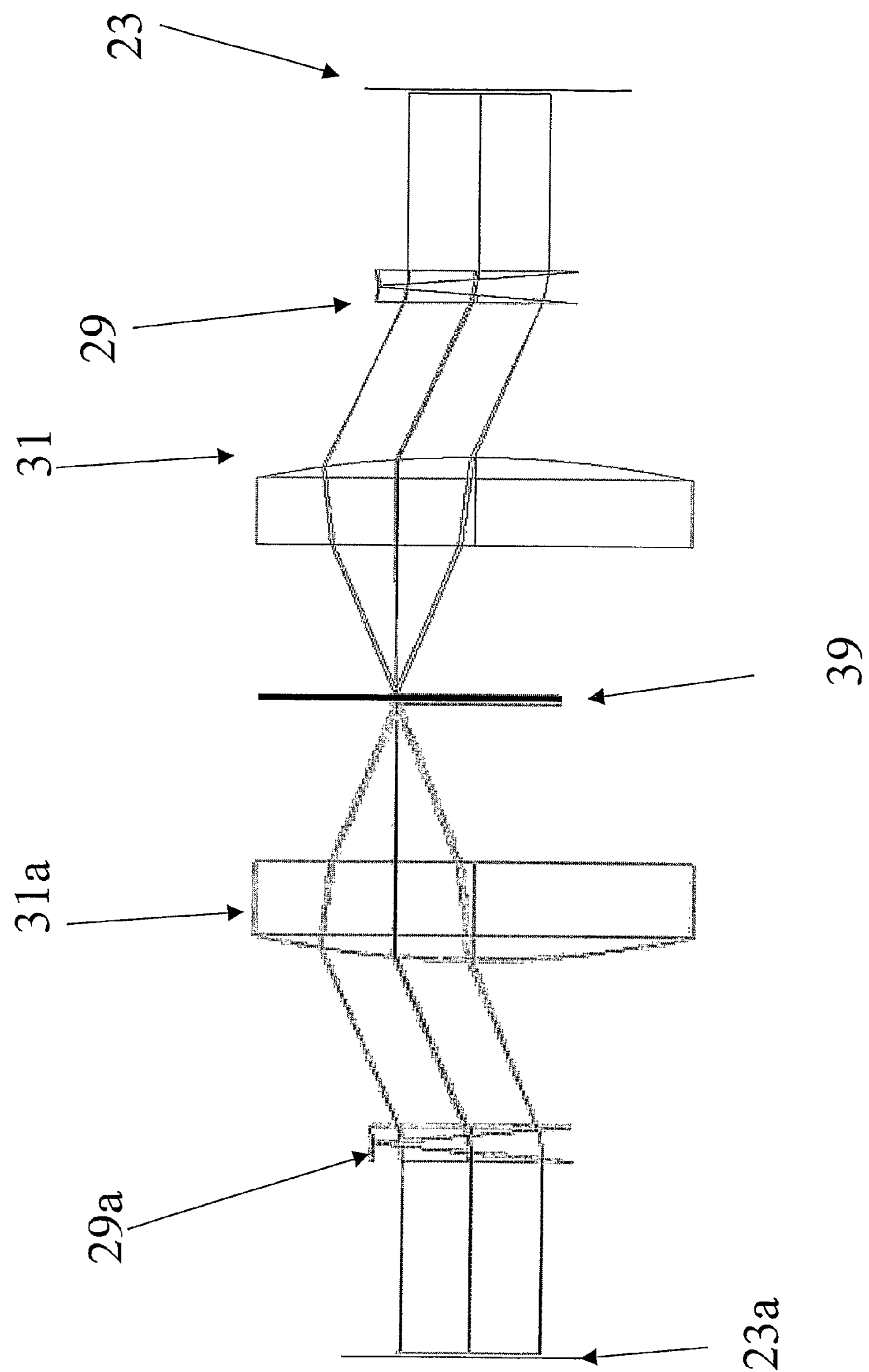
Figure 5:
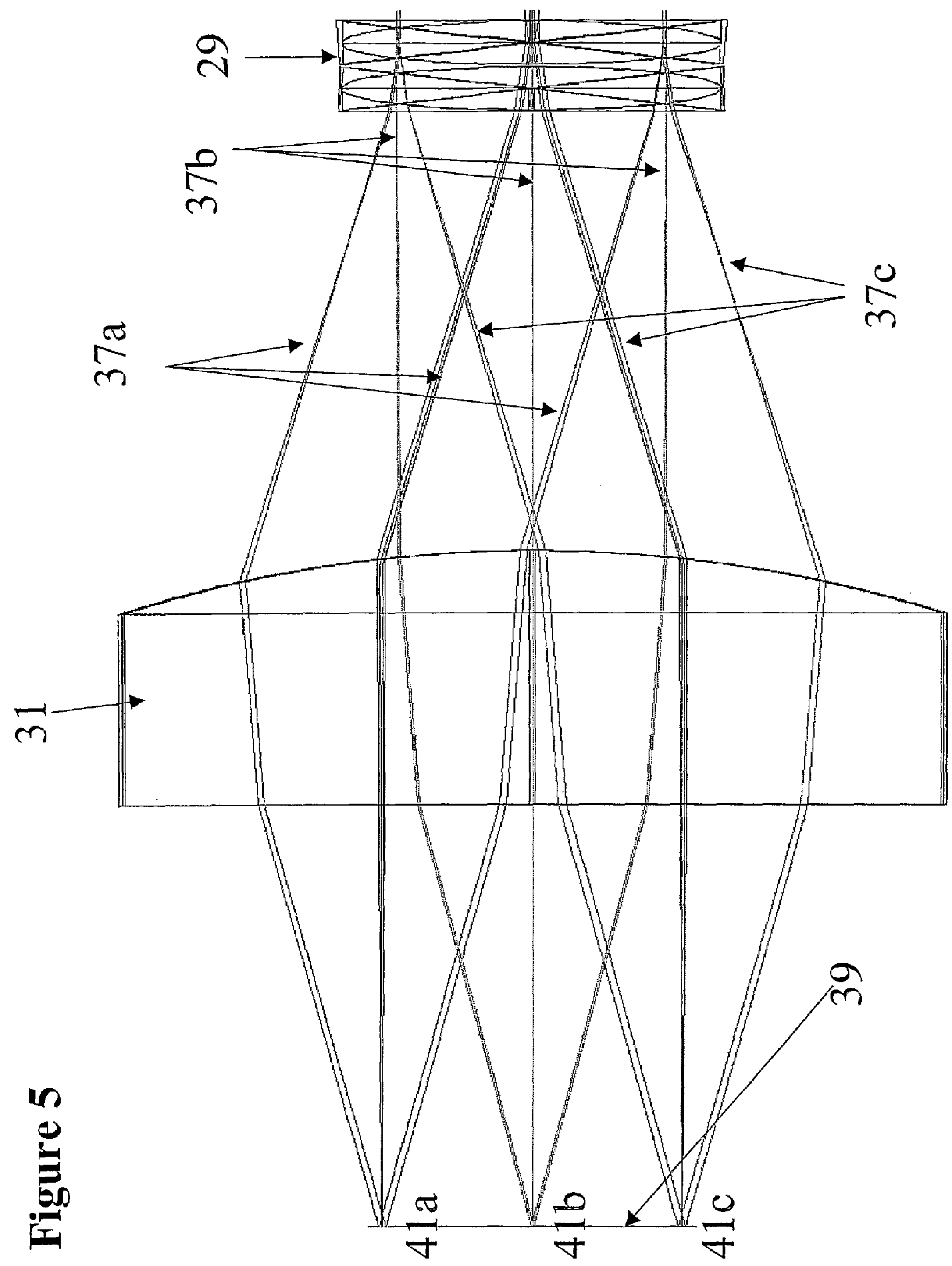
Figure 6A:
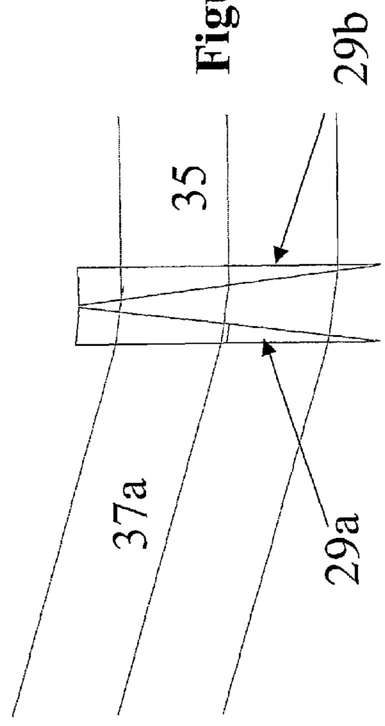
Figure 6B:
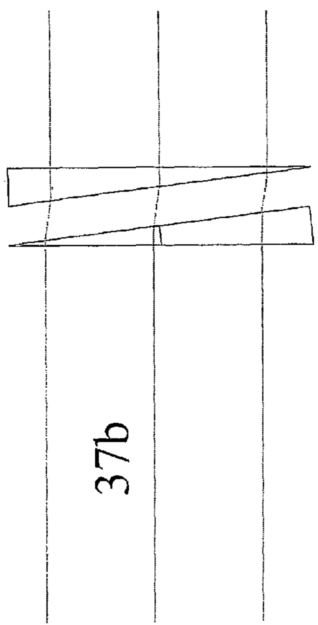
Figure 6C:
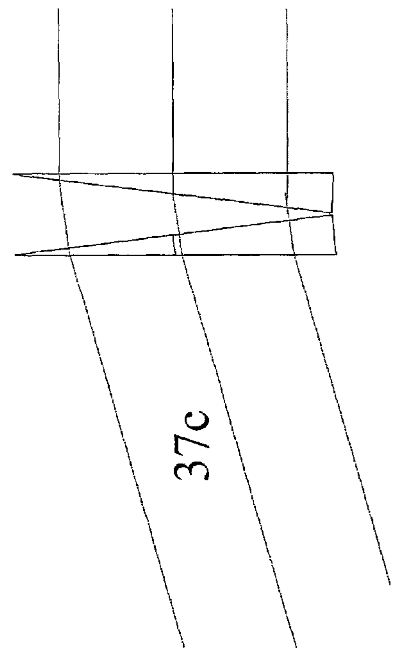
Figure 7A:
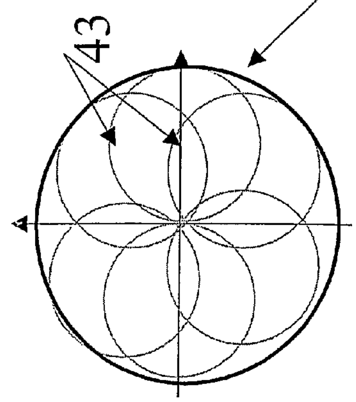
Figure 7B:
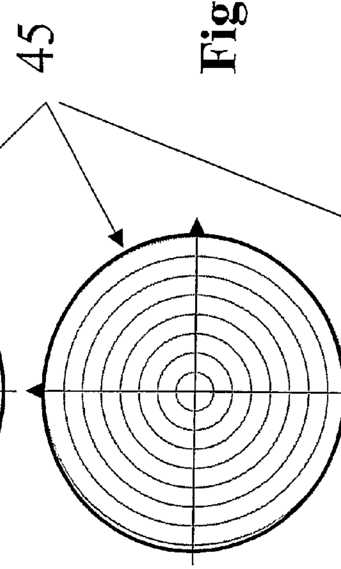
Figure 7C:
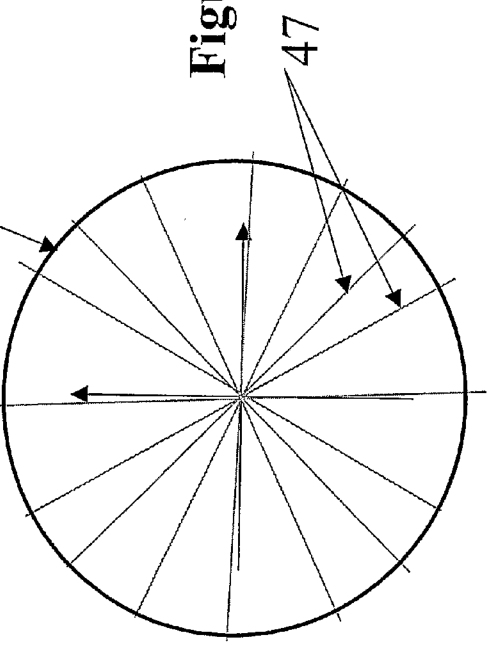
Figure 8:
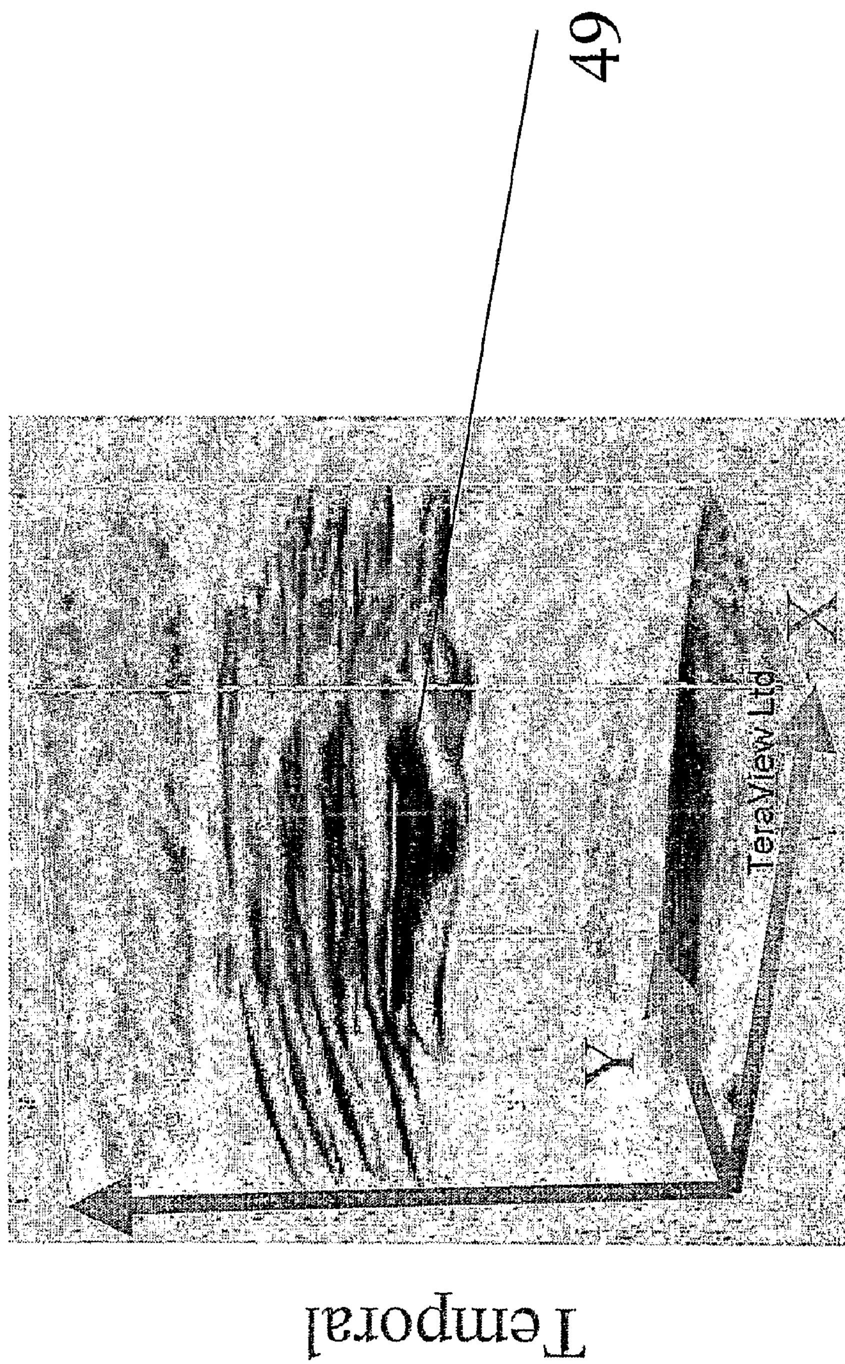
Figure 9B:
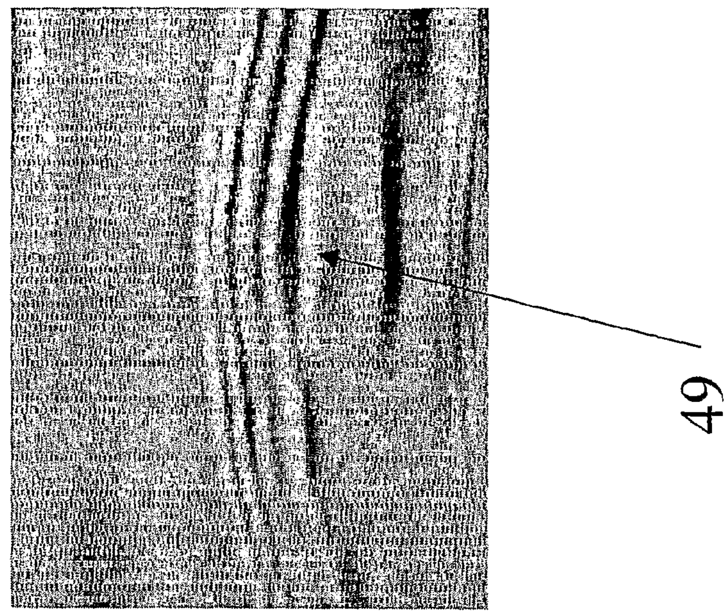
Figure 9A:
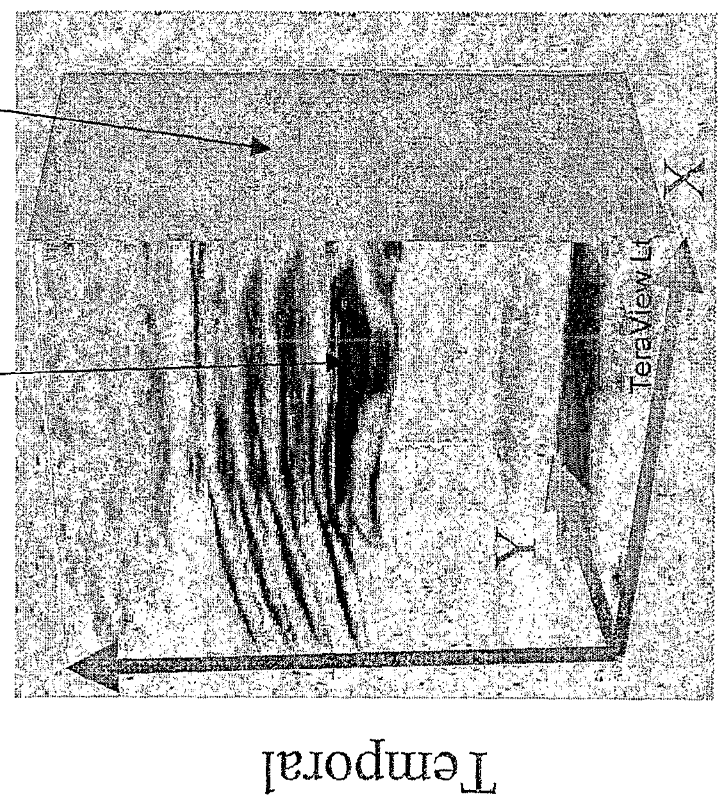

FIGS. 2 and 3 show typical apparatus configurations for THz imaging systems FIG. 4*a* shows an imaging system (configured to detect reflected radiation from an object) according to the present invention FIG. 4*b* shows an imaging system (configured to detect transmitted radiation from an object) according to the present invention FIG. 5 shows the THz optics of the apparatus of FIG. 4*a* in greater detail FIGS. 6*a*, 6*b* and 6*c* show part of the THz optics of FIG. 4*a* in further detail FIG. 7 shows different scanning modes of Risley prisms FIG. 8 shows a typical 3D data set of an object containing hidden plastic explosive FIGS. 9*a* and 9*b* show scan results from a typical prior art system.

Figure 10B:
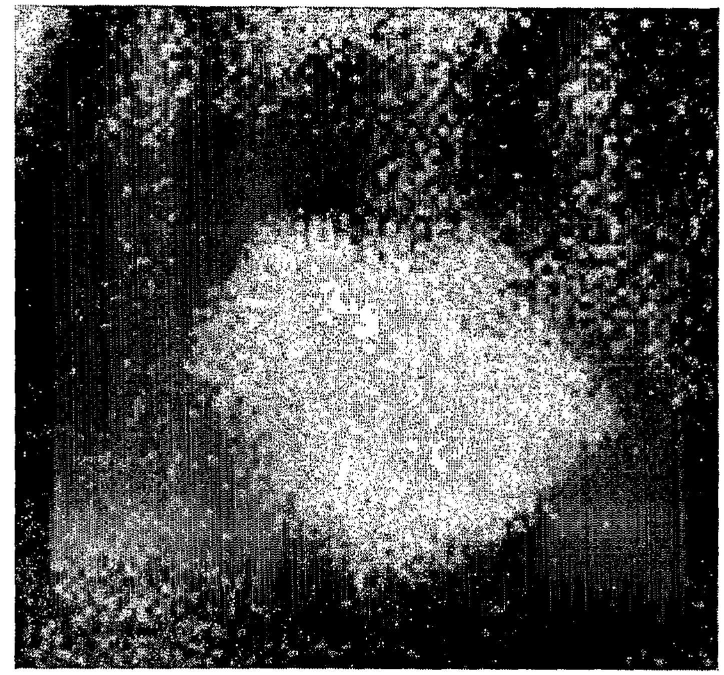
Figure 10A:
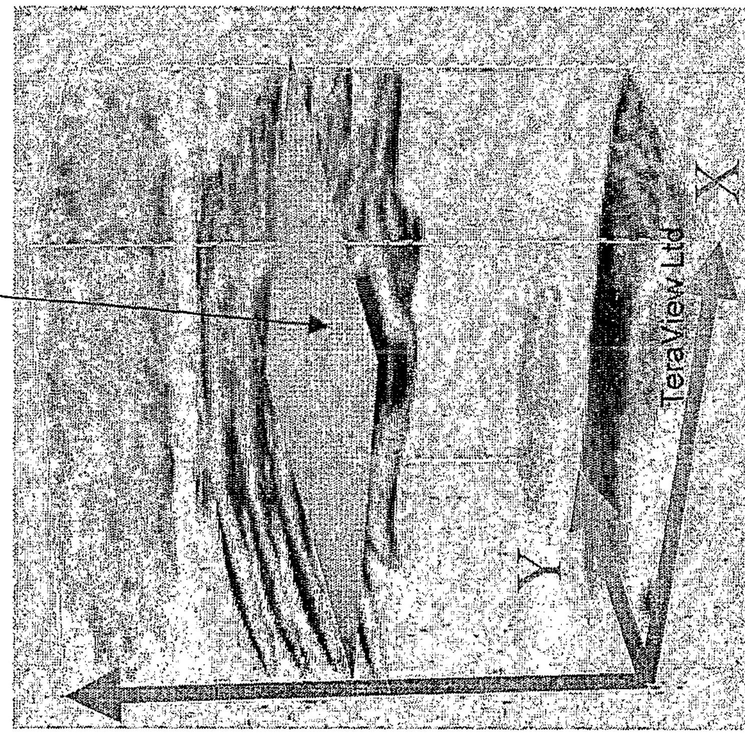
Figure 11B:
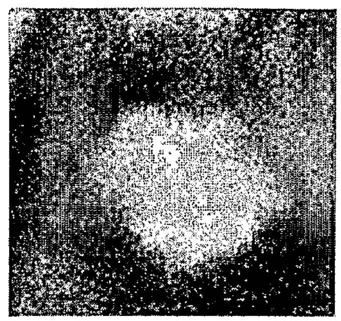
Figure 11C:
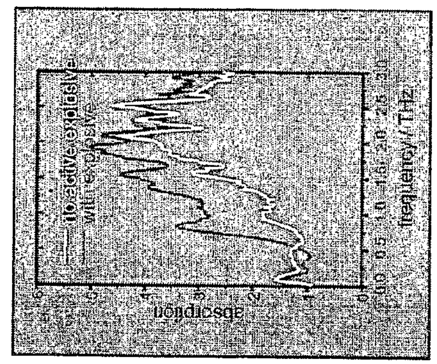
Figure 11A:
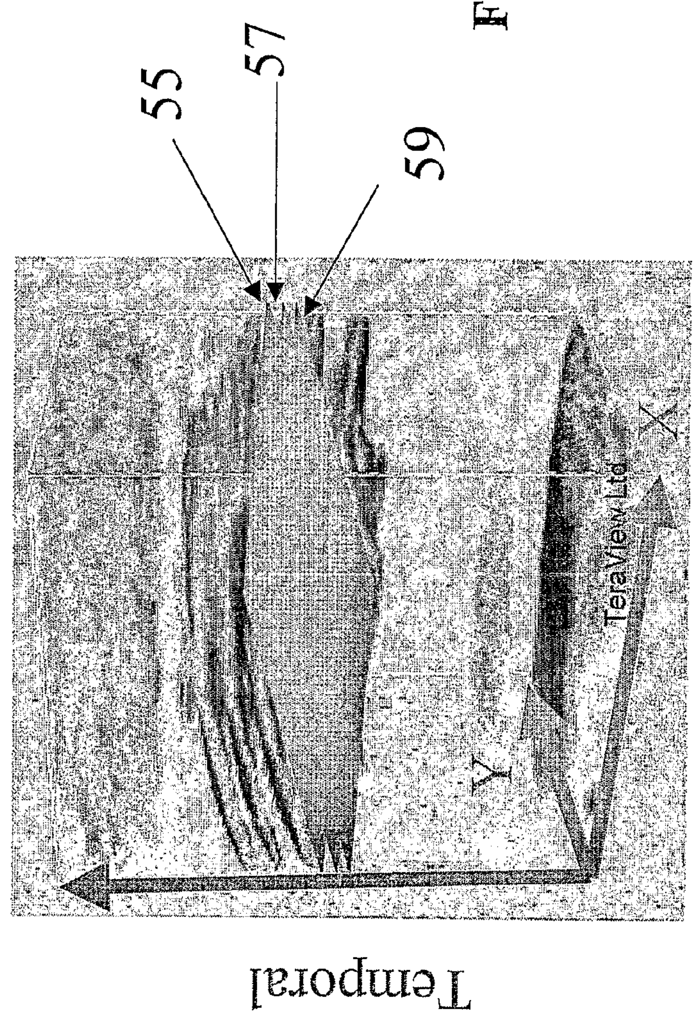
Figure 12B:
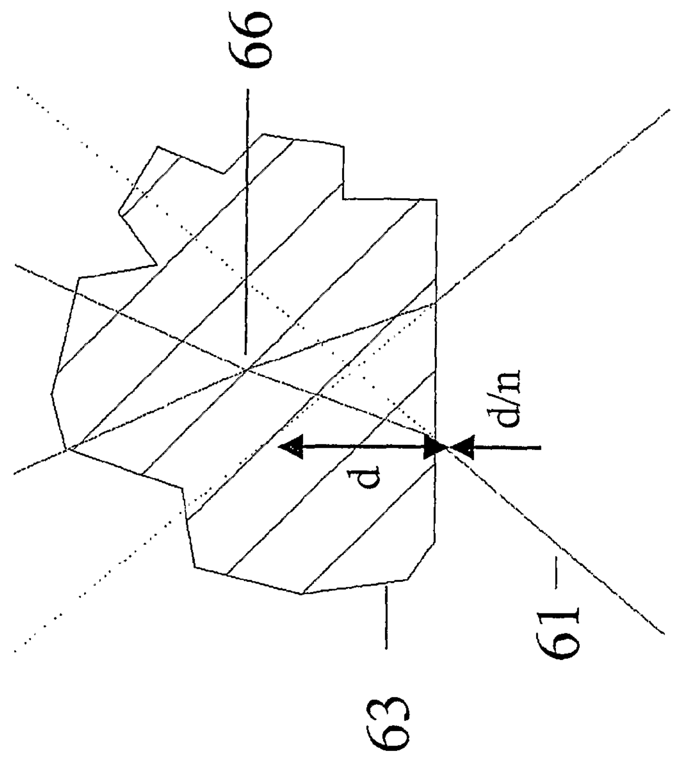
Figure 12A:
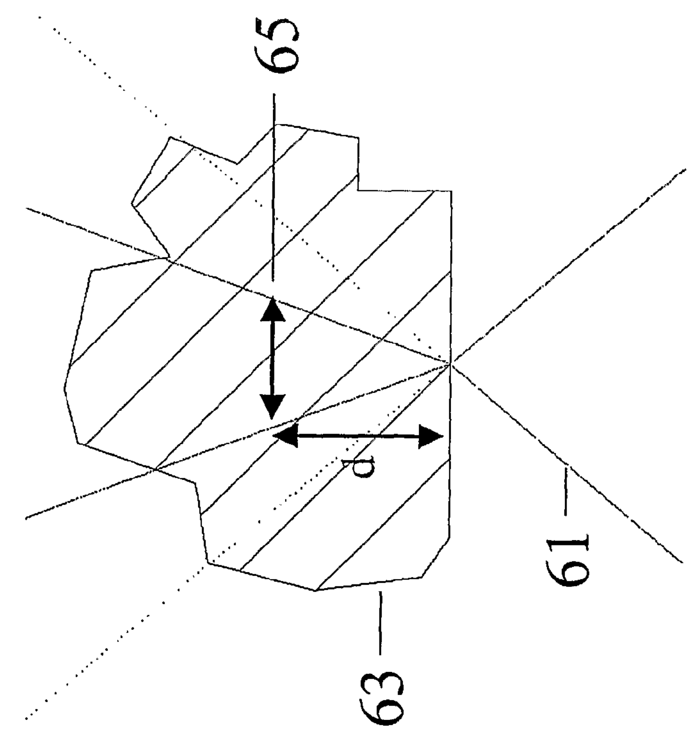
Figure 13:
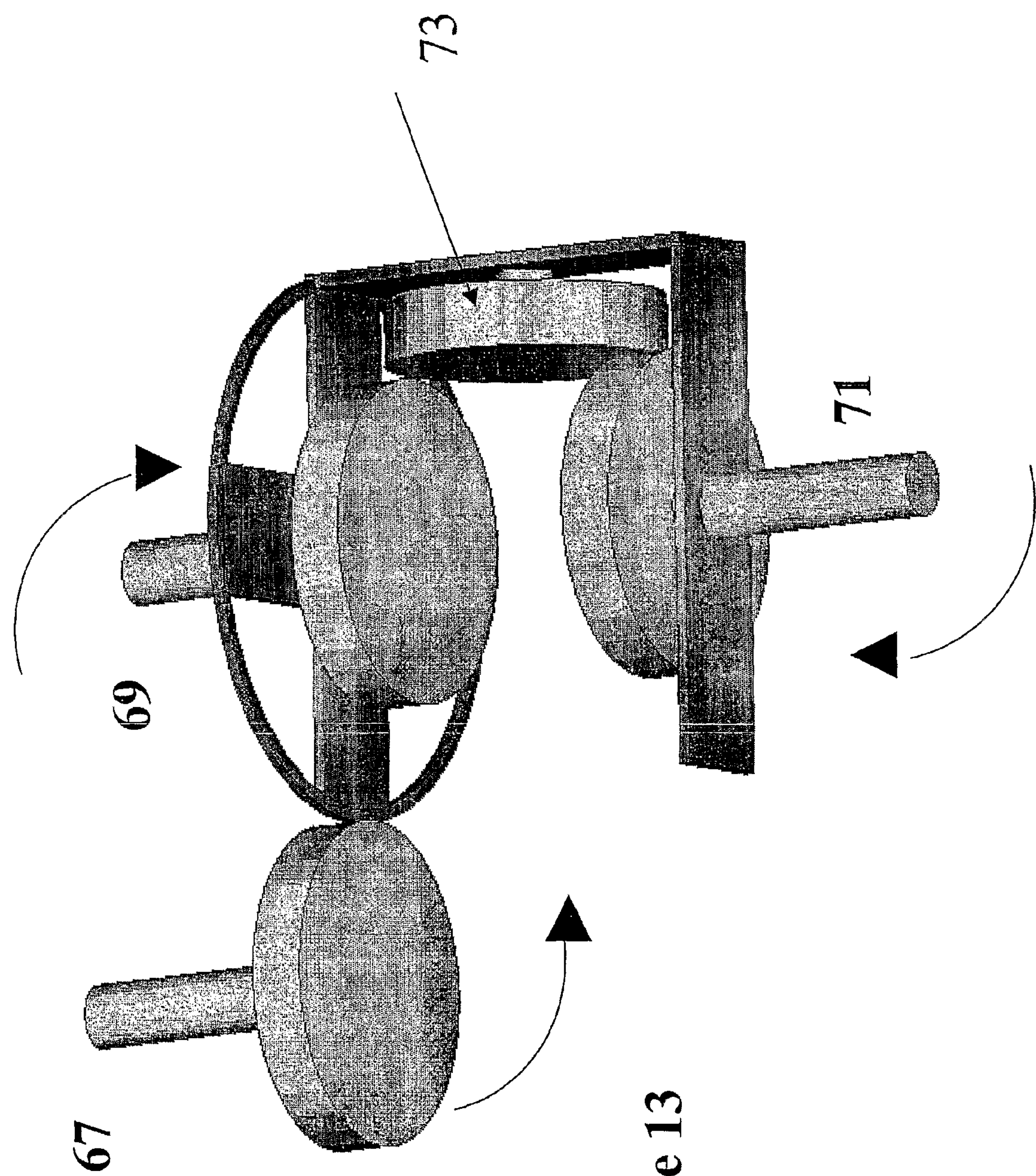
Figure 14:
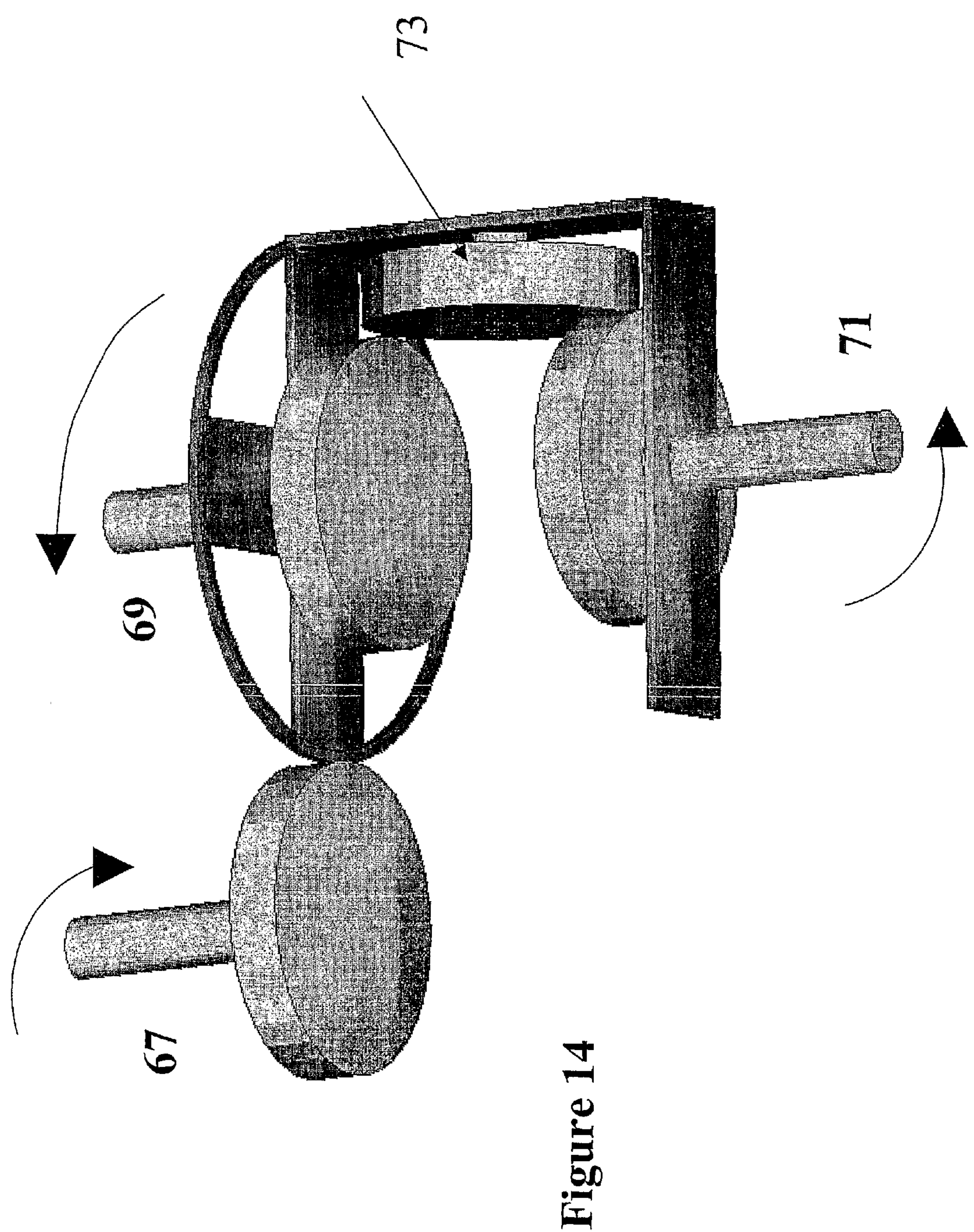

FIGS. 10*a* and 10*b* show scan results from a system according to the present invention FIGS. 11a, 11b and 11c show further scan results from a system according to the present invention FIGS. 12a and 12b show the effect that the depth of focus has on the resolution of THz imaging systems FIGS. 13 and 14 show a differential gear arrangement for driving the two prisms of a Risley prism.

Turning to FIG. 1, a schematic of a typical configuration for a THz imaging system is shown in which radiation is generated from a THz generator 1. THz generator 1, generates terahertz radiation in the range from 0.025 THz to 100 THz (the generated radiation could be a pulse comprising a plurality of frequencies in this range or alternatively a continuous wave beam of radiation at a single frequency). The THz radiation emitted from the generator 1 irradiates sample 3.

The beam of radiation emitted from generator 1 is capable of being moved across the sample 3 in the x and y directions. The x and y directions being taken as two orthogonal directions which are substantially perpendicular to the path of the incident irradiating radiation from the source 1.

Sample 3 will both transmit and reflect radiation. In the specific example of FIG. 1, the sample is only shown to reflect radiation and only reflected radiation will be detected. However, transmission measurements are possible.

The reflected radiation is detected by detector 5. Optics 4a and 4b guide the radiation emitted from the source 1 to the sample 3 and radiation reflected from the sample 3 to the detector 5.

The detector 5 is used to detect both the amplitude and phase of the radiation emitted from the sample 3. In order to do this, there is a phase coupling/control means 7 provided between the detector (or an input to the detector) and the generator 1 or an input/output from generator 1. This phase control/coupling means will either provide the detector with a parameter corresponding to a phase input which can be varied relative to the source beam or it will vary the phase of the source beam with respect to a probe beam which will be supplied to an input of the detector.

Typically, a beam, a 'probe beam' 9 with a known phase relationship to that of the imaging radiation is fed into the phase coupling/control means 7. The phase coupling control means will typically comprise a variable optical path line which will allow the path length of the probe beam to be varied.

In many cases, the probe beam will be combined with the THz radiation which is reflected by (or transmitted through) the sample 3. One particularly popular way is to use electro-optic sampling (EOS), a detailed explanation of which is contained in Applicant's patent/application GB2359716.

An alternative detection technique is photoconductive detection as described by Martin van Exter and Daniel R. Grischkowsky, IEEE. trans. Microwave Theory, Vol. 38, No. 11, November 1990.

FIG. 2 shows the system components of a THz imaging system in more detail. This Figure shows a system comprising a THz source 11, an optical subsystem 13, a sample 15 and a detector 17. Optionally the system can include a reference window 19 which is located in close proximity to or in direct contact with the sample 15. The reference window can be used as a known feature to help interpret the detected radiation and can also provide protection for the optical subsystem and other system elements. In some arrangements the reference window is incorporated into a sample enclosure means in order to allow the sample to be probed under various special atmospheres.

The path of the THz beam 21 is shown from the emitter 11 to the detector 17. It can be seen that the configuration shown in FIG. 1 relates to a reflection based system.

In order to scan the object 15 prior art systems have either generally moved the sample 15 (as indicated in reference to FIG. 1) or moved the entire imaging system (11, 13, 17). In either case this involves moving relatively massive objects which limits the scanning speed across the sample.

FIG. 3 shows a transmission based system. Like features compared to the system shown in FIG. 2 are depicted by like numerals. In this configuration the emitted beam passes through the sample 15 to the detector 17. If beam scanning is required then similar considerations to those mentioned above apply.

FIG. 4a shows an embodiment according to the present invention comprising a THz source 23, a detector 25 and an object to be scanned 27. Beam positioning is achieved by means of an optical subsystem (29, 31) which comprises two elements, a so-called Risley prism 29 and a telecentric lens 31. The Risley prism is a device known in the art (see for example, WO92/03187) and generally comprises a pair of prisms 29a, 29b. A beam splitter 33 is used to direct radiation to the detector 25.

The pair of prisms comprising the Risley prism 29 are mounted serially in the path of the emitted radiation such that the planes bisecting the apex angles of the individual prisms (29a and 29b) are substantially parallel to one another and are substantially normal to the direction 35 of the incident radiation.

In use emitted radiation is incident on the Risley prism 29. One or both of the prisms of the Risley prism can be rotated about an axis in order to angularly deflect the emitted radiation beam. The rotation axes for the two prisms are usually coincident and are parallel to the direction of the incident source radiation (hereinafter this axis will be referred to as the "rotation axis").

Following interaction with the Risley prism, the deviated beam 37 is then incident on the second optical element 31, the telecentric lens. The telecentric lens 31 focuses the deviated beam onto an image plane 39 (which is where the sample is located). The lens 31 produces a substantially flat image plane 39.

As the relative position of the prisms 29a and 29b changes, the angular deviation of the beam 37 changes. The position that this deviated radiation is incident on the lens 31 therefore moves and as a consequence the focus point moves to different positions on the image plane 39 which allows plane sections through the sample 27 to be imaged.

Radiation reflected from the sample passes back through the lens 31 and the prism 29 to the beam splitter 33 where it is directed into the detector 25 (which in this example is positioned in an off axis location).

As stated above the telecentric lens will convert the angular deviation of the THz souce beam into lateral sweep of a focused beam on a flat image plane. If the THz source beam axis and that of the telecentric lens coincide (as is the case in this Figure) then the reflected radiation traces back along the path of the source beam. This is why the beam-splitter is required. However, if the THz source beam is offset with respect to the telecentric lens then the beam will focus at a constant angle to the image plane and the reflected light will trace a path back through the optical system parallel to, but offset from the THz source beam.

An example of the configuration shown in FIG. 4a was constructed using a plano-spherical silicon lens (radius of curvature 121.72 mm, 25 mm thick) as the telecentric lens. The Risley prism was placed 43.4 mm from telecentric lens (distance from the front face of the silicon lens to the surface of the prism 29a in the Risley prism) and the THz beam was brought to a focus 41.7 mm from the back of the lens. The silicon lens produced a lateral scan of 25 mm. With an input beam of 25 mm in diameter the lens produced a geometric RMA spot radius of less than 153 μm.

The Risley prism in the constructed example consisted of two circular 7 degree wedged z-cut quartz prisms (35 mm in diameter and 4.5 mm at maximum thickness). Quartz was chosen for its low reflection, low absorption losses and low dispersion. Quartz also has the advantage that it is transparent to visible wavelengths of light and so its performance can be readily checked with laser diodes. The prisms were arranged to give an angular displacement of up to 14 degrees, i.e. an arc of 28 degrees maximum could be produced.

The faces of the prisms were arranged to be adjacent to minimise interference reflections.

FIG. 4*b* shows an arrangement similar to that depicted in FIG. 4*a*. In FIG. 4*b* however the optics are configured for detecting transmitted radiation (as opposed to the reflection configuration of FIG. 4*a*). Like numerals denote like features.

It can be seen from FIG. 4*b* that a further set of optics are present on the opposite side of the sample to the emitter 23. This further set of optics comprises a telecentric lens 31*a* and Risley prism 29*a* (It can be seen from FIG. 4*b* that the arrangement of FIG. 4*a* has been mirrored about the image plane).

In use, radiation from the emitter 23 passes through the Risley prism 29 and telecentric lens 31 as described in relation to FIG. 4*a*. Radiation that is transmitted through the sample is then directed by a second telecentric lens 31*a* (the "third optical element") onto a second Risley prism 29*a* (the "fourth optical element"). The second Risley prism 29*a* then directs the received radiation to a detector 23*a*.

FIG. 5 shows the Risley prism 29 and telecentric lens 31 arrangement from FIG. 4 in more detail (like numerals being used to denote like features). As the individual prisms within the Risley prism rotate the incident radiation beam is angularly deflected to different locations. The Figure shows three ray traces, 37*a*, 37*b*, 37*c*. As the deviated beam passes through the telecentric lens 31 these three angular deviations are converted to different locations (41*a*, 41*b* and 41*c* respectively) on the image plane 39.

FIGS. 6*a*, 6*b* and 6*c* show the prism 29 depicted in FIGS. 4 and 5 in more detail (again like numerals from FIGS. 4 and 5 are used to denote like features). In this example both prisms 29*a* and 29*b* within the Risley prism can rotate about the rotation axis.

In FIG. 6*a*, the two prisms are configured such that their thick ends are together at the top of the diagram. The deviations produced by the two prisms adds such that the beam 35 (from the source) is deviated towards the top of the page as shown by trace 37*a*.

In FIG. 6*b* the thick ends of the wedge are now directly opposite one another (i.e. thick end of 29*b* is at top of page and thick end of 29*a* is at bottom of page). The deviations produced by the two prisms cancel each other and the beam 35 is now substantially unaffected by its passage through the prism, as shown by trace 37*b*.

In FIG. 6*c*, the two prisms are now arranged such that their thick ends are together at the bottom of the diagram. The deviations produced by the two prisms adds once again but this time the beam 25 is deviated towards the bottom of the page as shown by trace 37*c*.

FIGS. 7*a*, 7*b* and 7*c* depict the various actions of the Risley prism and the possible scanning modes.

If one of the prisms 29*a*, 29*b* is held motionless while the second is rotated about the rotation axis then the emergent beam will perform a conical sweep. If the deflected beam is projected onto a screen then the beam will be seen to project a circle which is offset from the rotation axis and at an angle determined by the position of the motionless prism. A series of such circles 43 are shown in FIG. 7*a*. In this Figure (and also FIGS. 7*b* and 7*c*) the rotation axis is perpendicular to the plane of the page.

The entire potential scanning area (as depicted by the circle 45) can be scanned by rotating one prism quickly and rotating the other prism slowly (as opposed to holding it motionless). In this case an offset circle 43 drawn by the first prism is itself swept in a circle about the rotation axis and the entire area 45 can be scanned.

FIG. 7*b* shows the case where both prisms are rotated together. In this case a circle is again produced. The radius of the circle is determined by the relative positions of the prisms to one another.

However, if there is a velocity offset between the two prisms (instead of rotating the two prisms at the same angular speed) then the beam will trace a spiral and once again the entire scan area 45 can be scanned.

FIG. 7*c* shows the case where there is exact counter rotation of the two prisms. The resultant sweep in this case is a reciprocating lateral motion. Depending on the starting positions of the prisms the orientation of the lateral sweep can be altered (see traces 47). If, once again, one of the prisms is slowed slightly (instead of having exact counter rotation) then the lateral sweep will rotate slightly about the rotation axis from one sweep to the next. In this way successive sweeps will walk their way across the entire area 45.

FIGS. 7*a-c* describe the basic actions of the Risley prism. More complex patterns including polygons, ellipses and crescents are possible (see for example, Optical Scanning: Design and Applications, Proceedings of the Society of Photo-optical Instrumentation Engineers (SPIE) 3787, pp 74-86, 1999).

The three modes described above have various advantages. The spiral sweep has the advantage that it can cover a circular area of any given radius within the largest circle possible. The lateral walk must travel across the entire width of the largest circle but does allow for a simple one-dimensional scan. The swept circle is the simplest mechanically since the two prisms do not require careful synchronisation as in the other two modes. Furthermore, in the swept circle mode only one of the prisms needs to be rotated quickly—the second prism can be arranged to rotate more slowly—and this further reduces the mechanical constraints on the system.

It should be noted that although the three modes described above are the primary modes a continuum of slight variations exist between them.

The advantages of the Herschel/Risley prism system according to the present invention are that the prisms comprising the Risley element are continuously spun and so do not suffer from the high inertial acceleration issues as the prior art systems (for example, tilting mirror subassemblies). Further the optical subsystem according to the present invention is compact in comparison to prior art systems.

FIG. 8 shows a typical three dimensional data set of an object imaged using a THz imaging system. The spatial and temporal axes are clearly marked and it should be noted that the temporal axis corresponds to the direction of the scanning radiation and so effectively relates to depth of the sample. The feature indicated 49 relates to hidden plastic explosive within the object.

As mentioned in connection to FIG. 1 above, THz imaging is an inherently phase sensitive imaging technique and many THz imaging systems rely on optical delay lines to acquire phase information. Since the components of the delay line are often smaller and lighter than the THz optics it is common to quickly scan the phase and move object or the THz optics more gradually.

FIG. 9*a* shows, compared to the fully rendered scan of FIG. 8, the portion of data that varying the optical delay line will capture. The shaded region 51 indicates that a two dimensional slice through the sample, parallel to the direction of the imaging radiation, is imaged via this technique (Note: that to image the whole of this shaded area either the sample or the optics will need to be moved slightly in the y direction). FIG. 9*b* shows the processed image information relating to this two dimensional slice.

FIG. 10*a* shows a main advantage of the method and apparatus of the present invention over prior art imaging systems. In this case, the temporal depth of the scan is fixed (e.g. by keeping the optical delay line at a constant path length) and a cross-sectional scan 53, perpendicular to the imaging radiation, is taken through the sample. FIG. 10*b* shows the processed image information relating to the cross-sectional scan of FIG. 10*a*.

The apparatus and methods of the present invention may also be used to perform three dimensional scans over limited sample thicknesses. This is achieved by scanning the delay line of an imaging system through a small delay (which equates to a certain sample thickness) in order to obtain a horizontal scan which has limited spectral data. An example of such a three dimensional scan is shown in FIGS. 11*a*, 11*b* and 11*c*.

FIG. 11*a* shows a number of two dimensional cross-sectional scans made at various depths in the sample, see x-y slices 55, 57, 59. Combining the scan information from these slices results in the image of FIG. 11*b*.

FIG. 11*c* shows the spectral information obtained from such a "limited depth scan". The presence of explosive is clearly distinguishable from a sample containing no active explosive.

FIGS. 12*a* and 12*b* show the effect that the depth of focus has on the resolution of THz imaging systems. In FIG. 12*a* a prior art system which scans by varying the optical delay path is shown. The source beam 61 of THz radiation is focussed on the surface of the object 63 under investigation and it can be seen that as a result of refraction effects at the surface of the object imaging at a depth d can only be achieved to a limited resolution 65.

FIG. 12*b* shows an embodiment of the present invention. Here the source radiation 61 is not focussed on the surface but at a depth d by the optical subsystem of the invention. The resolution 66 of the object 63 at depth d is now more accurate than the prior art. It should be noted that since the object has a refractive index of n and air has an index, n=1, then to move the focus within the object by a distance d only requires the focussing optics to be moved by a distance d/n.

FIGS. 13 and 14 show a differential gearing arrangement for driving the two prisms of the Risley prism element. In both Figures axles 69 and 71 are connected by a gearing arrangement (not shown) to the two prisms (also not shown).

Axle 67 can be driven in either a clockwise or anticlockwise direction in order to drive the axles 69 and 71 as shown. In the examples of FIGS. 13 and 14 the arrangement is set up to drive axles 69 and 71 in opposite directions to one another. The replacement of cog 73 with two separate cogs would allow the axles 69 and 71 to be driven in the same direction.

If both Axles 67 and 69 are driven then the movement of axle 71 will be the combination of 67 and 69. This would therefore introduce a velocity offset into the two prism system. In this instance only one of axles 67 or 69 would need to be driven at high speed.

The invention claimed is:

1. An apparatus for investigating a sample comprising:

a source of beam radiation a detector for detecting a beam of radiation reflected by the sample and for receiving a probe beam, the probe beam having a phase related to the phase of the beam of radiation irradiating the sample;

a delay line being operable to vary the relative path lengths of the probe beam and the beam of radiation irradiating the sample; and an optical subsystem for manipulating the beam between source and detector wherein the optical subsystem comprises a first optical element arranged in use to angularly scan the source beam through a plurality of angles within a given solid angle and a second optical element arranged to focus the beam from the first optical element onto a substantially flat image plane, wherein radiation reflected by the sample passes back through the first and second optical elements to the detector, and wherein the detector is configured to detect radiation reflected at varying depths within the sample by varying the relative path lengths of the probe beam and the beam of radiation irradiating the sample using the delay line.

2. An apparatus according to claim 1 wherein the first optical element comprises a first prism and a second prism mounted serially in the path of the radiation emitted from the source, the prisms being arranged such that a first plane bisecting the apex angle of the first prism is substantially parallel to a second plane bisecting the apex angle of the second prism, the first and second planes both being substantially normal to a rotation axis corresponding to the direction of radiation incident upon the prisms from the source.

3. An apparatus according to claim 2 wherein at least one of the pair of prisms is rotatable about the rotation axis.

4. An apparatus according to claim 3 wherein each prism is mounted within a prism holder and each holder forms part of a drive mechanism capable of rotating the prism.

5. An apparatus according to claim 4 wherein each holder is under computer control.

6. An apparatus according to claim 2 wherein both prisms are capable of rotation about the rotation axis.

7. An apparatus according to claim 6 wherein the pair of prisms are capable of rotation relative to one another about the rotation axis.

8. An apparatus according to claim 1 wherein the second optical element comprises a telecentric lens.

9. An apparatus according to claim 8 wherein the telecentric lens has a symmetrical axis which is coincident with a rotation axis of the first optical element.

10. An apparatus according to claim 8 wherein the first optical element comprises a diffraction grating or a dispersive prism.

11. An apparatus according to claim 8 further comprising means for analysing the detected radiation by Fourier transform.

12. A method for investigating a sample comprising the steps of:

irradiating the sample by angularly scanning a source beam through a plurality of angles within a given solid angle using a source of radiation with a frequency in the range 25 GHz to 100 THz, the radiation capable of being focused at any given point within a plane through the sample, said plane being substantially normal to the direction of the irradiating radiation, and detecting said radiation reflected from a depth within the sample, wherein detecting said radiation comprises receiving a probe beam having a phase related to the phase of the beam of radiation irradiating the sample and controlling the depth within the sample by varying the relative path lengths of the probe beam and the beam of radiation irradiating the sample.

13. A method for investigating a sample according to claim 12 wherein the source beam passes through an optical subsystem which angularly scans the source beam and then focuses the source beam onto a flat image plane and wherein the radiation detected from the sample is detected via the optical subsystem.

* * * * *